United States Patent [19]

Loozen

[11] Patent Number: 5,272,140
[45] Date of Patent: Dec. 21, 1993

[54] 11-ARYL STEROID DERIVATIVES

[75] Inventor: Hubert J. J. Loozen, Uden, Netherlands

[73] Assignee: Akzo N.V., Arnhem, Netherlands

[21] Appl. No.: 488,391

[22] Filed: Feb. 27, 1990

Related U.S. Application Data

[63] Continuation of Ser. No. 146,895, Jan. 22, 1988, abandoned.

[30] Foreign Application Priority Data

Jan. 23, 1987 [NL] Netherlands ............... 8700157

[51] Int. Cl.$^5$ ............... A61K 31/58; A61K 31/585; A61K 31/56; C07J 9/00; C07J 3/00; C07J 7/00; C07J 1/00
[52] U.S. Cl. ............... 514/172; 514/173; 514/174; 514/175; 514/177; 514/178; 514/179; 552/508; 552/540; 552/544; 552/546; 552/548; 552/552; 552/553; 552/554; 552/555; 552/557; 552/598; 552/608; 552/611; 552/642; 552/650
[58] Field of Search ............... 514/172, 173, 175, 177, 514/179, 174, 178; 552/508, 540, 544, 546, 548, 552, 553, 554, 555, 557, 598, 608, 611, 642, 650

[56] References Cited

U.S. PATENT DOCUMENTS

| | | | |
|---|---|---|---|
| 4,233,296 | 11/1980 | Teutsch et al. | 514/172 |
| 4,386,085 | 5/1983 | Teutsch et al. | 260/397.45 |
| 4,447,424 | 5/1984 | Teutsch et al. | 260/397.45 |
| 4,519,946 | 5/1985 | Teutsch et al. | 260/397.45 |
| 4,536,401 | 8/1985 | Neef et al. | 514/173 |
| 4,540,686 | 9/1985 | Philibert et al. | 514/179 |
| 4,609,651 | 9/1986 | Rohde et al. | 514/179 |
| 4,634,695 | 1/1987 | Torelli et al. | 260/397.45 |

FOREIGN PATENT DOCUMENTS 3231827  8/1982  Fed. Rep. of Germany ............... 260/397.47

OTHER PUBLICATIONS

Chemical Abstracts, vol. 100 (1984) #68601k; Philibert et al.
Chemical Abstracts, vol. 102 (1985) #24921b; Neef et al.
Teutsch et al. CA 90:6615j (1979).
Rohde et al. CA 104:186715f (1986).
Ottow et al, *Steroids*, vol. 44, No. 6, Dec. 1984, pp. 519-530.

*Primary Examiner*—Frederick E. Waddell
*Assistant Examiner*—Kimberly R. Jordan
*Attorney, Agent, or Firm*—Donna Bobrowicz

[57] ABSTRACT

The invention relates to 11-aryl steroid derivatives, having the structure

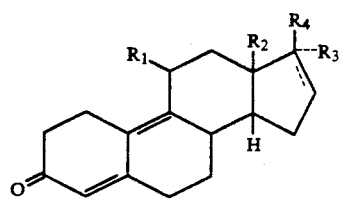

wherein:
$R_1$, $R_2$, $R_3$, and $R_4$ are as described in the specification
and to processes for their preparation and to pharmaceuticals comprising these compounds.

These compounds exhibit a strong anti-progestinic activity and a weak or non-existent anti-glucocorticoid activity.

10 Claims, No Drawings

11-ARYL STEROID DERIVATIVES

This is a continuation of application Ser. No. 07/146,895, filed Jan. 22, 1988, now abandoned.

The invention relates to new 11-aryl steroid derivatives, to methods for preparing said compounds and also to pharmaceutical products which contain said derivatives as active constituent.

Antiprogestins are substances which have affinity for the progesterone receptors, such substances not having, or having to a considerably reduced degree, the action of progesterone and/or which inhibit progesterone biosynthesis. Progesterone is involved, inter alia, in the implantation of a fertilized egg cell in the wall of the uterus. It will be possible to prevent implantation by occupying receptor sites in the cells pf the uterus and/or to inhibit progesterone biosynthesis with antiprogestins, as a result of which the pregnancy can be terminated at a very early stage. Antiprogestins are known from the European Patent Application 0,057,115 and the German Offenlegungsschrift DE 3,413,036.

It has been found however that, in addition to the desired antiprogestinic activity, such antiprogestins also have an antiglucocorticoid activity which is not desirable if said substances are used as a pregnancy-terminating agent.

A new group of compounds has now been found which have a strong antiprogestinic and a weak or non-existent antiglucocorticoid activity.

The invention therefore relates to steroids having the following formula:

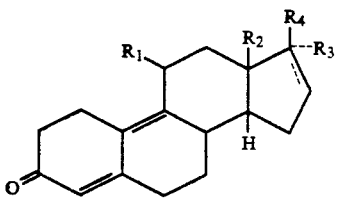

wherein
$R_1$ is a homocyclic or heterocyclic aryl group having one of the following substituents: an optionally saturated or unsaturated, branched or unbranched hydrocarbon radical containing 1-10 carbon atoms, the hydrocarbon radical being optionally provided with a hydroxyimino, oxo and/or hydroxyl group, or a

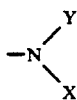

group, where X and Y are each separately H or a hydrocarbon (1-4 C) radical or are together a hydrocarbon (2-6 C) radical;

$R_2$ is an alkyl group containing 1-4 carbon atoms;

$R_3$ is H, OH, a saturated or unsaturated hydrocarbon radical containing 1-8 carbon atoms, optionally provided with one or more hydroxyl, azido, nitrile, oxo and/or halogen groups, or is a (1-18 C) acyloxy or (2-8 C) alkoxyalkyl or (1-18 C) acyl or (1-12 C) alkoxy group;

$R_4$ is an H, OH, a saturated or unsaturated hydrocarbon radical containing 1-8 carbon atoms, optionally provided with one or more hydroxyl, azido, nitrile, oxo and/or halogen groups, or is a (1-18 C) acyloxy or (2-8 C) alkoxyalkyl or (1-18 C) acyl or (1-12 C) alkoxy group; or $R_3$ and $R_4$ together form a ring system or an alkylidene group having 1-6 carbon atoms and the dotted line represents an optional bond between the carbon atoms 16 and 17 of the steroid skeleton, with the proviso that $R_3$ or $R_4$ is absent if said bond between said carbon atoms 16 and 17 is present.

The aryl group in $R_1$ may be derived from, for example, benzene, biphenyl, naphthalene, anthracene, phenanthrene, or a heterocyclic aromatic compound such as pyridine, thiazole, thiophene, pyrrole, furan, benzothiophene, benzofuran, pyrimidine, pyrazine, purine and imidazole.

If the aryl group is not heterocyclic, preference is given to the phenyl group. If the aryl group is heterocyclic, preference is given to nitrogen- and/or sulphur-containing heterocyclic groups, such as those derived from pyridine, pyrrole, thiazole, thiophene, benzothiophene, pyrimidine, pyrazine, purine and imidazole. Phenyl is the most preferred. In the case of a phenyl group, the substituent is preferably located in the meta or para position.

The substituent on the aryl group may be a branched or unbranched, saturated or unsaturated hydrocarbon radical containing 1-10 carbon atoms, optionally provided with a hydroxyimino, hydroxyl and/or oxo group, such as methyl, ethyl, propyl, isopropyl, hexyl, 3-methylheptyl, ethenyl, ethynyl, propenyl, acetyl, propionyl, hexanoyl, 1-hydroxyiminoethyl, 1-hydroxyiminopropyl, butyryl, formyl, 2-oxobutyl, hydroxymethyl, 3-hydroxyhexyl, hydroxyethyl and 8-hydroxyoctyl. Preferably, the hydrocarbon radical substituent on the aryl group is an acyl group having 1-4 carbon atoms.

The substituent on the aryl group may furthermore be a group with the formula:

If X and Y each separately are hydrocarbon radicals (1-4 C), such a radical may be methyl, ethyl, vinyl, ethynyl, propyl, 2-propenyl, allenyl, 1-propynyl, butyl or branched analogues thereof. If X and Y together form a hydrocarbon radical (2-6 C), said hydrocarbon group may be saturated or unsaturated; preferably, such hydrocarbon radical contains 4 or 5 carbon atoms. If X and Y do not together form a hydrocarbon radical preferably, X and Y are each separately H or a saturated alkyl group containing 1-3 carbon atoms . The most preferred substituents on the aryl group are an acyl group having 1-4 carbon atoms or a group

X and Y separately being H or a saturated alkyl group having 1-3 carbon atoms. $R_2$ is preferably ethyl or methyl and still more preferably methyl. The (1-8 C) hydrocarbon radical $R_3$ and $R_4$ may be, inter alia, methyl, ethyl, vinyl, ethynyl, propyl, 2-propenyl, allenyl, 1-propynyl, butyl, octyl or an analogue provided with one or more hydroxyl, azido, nitrile, oxo and/or halogen groups, such as 3-hydroxyl-1-propynyl, 3-hydroxy-1-propenyl, chloroethynyl, bromoethynyl and 3-hydroxypropyl. Preferably, the hydrocarbon radical optionally has been provided with a hydroxyl group.

The acyloxy or acyl group $R_3$ and $R_4$ is derived from an organic carboxylic acid containing 1-18 C atoms such as acetic acid, propionic acid, butyric acid, trimethylacetic acid, phenylacetic acid, cyclopentylpropionic acid, phenylpropionic acid, valeric acid, caproic acid, pelargonic acid, lauric acid, palmitic acid, benzoic acid or succinic acid.

The alkoxyalkyl group $R_3$ and $R_4$ preferably is a group having the formula $C_nH_{2n+1}OC_mH_{2m}$ wherein $n=1-4$ and $m=1-4$, like methyloxymethyl, butyloxybutyl or ethyloxymethyl. More preferably $n=1-3$ and $m=1-3$.

The alkoxy group $R_3$ and $R_4$ is derived from an ether containing 1-12 C atoms such as, for example, methyl ether, ethyl ether, cyclopentyl ether, benzyl ether and tetrahydropyranyl ether.

If $R_3$ and $R_4$ do not together represent a ring system, $R_3$ is preferably OH, (1-8 C) alkoxy, (1-6 C) acyl, (1-6 C) alkyl optionally provided With a hydroxyl group or alkoxyalkyl with the formula $C_nH_{2n+1}OC_mH_{2m}$ wherein $n=1-3$ and $m=1-3$ and $R_4$ is preferably H, (1-6 C) hydrocarbyl and $R_4$ together represent a ring system, preference is given to heterocyclic ring systems containing 5 atoms in the ring, the carbon atom at position 17 of the steroid skeleton being one of these 5 atoms and in particular, to heterocyclic ring systems comprising an oxygen atom in the ring which oxygen atom is bound to the carbon atom at position 17 of the steroid skeleton. The greatest preference is given to the following heterocyclic ring systems:

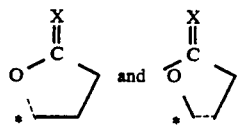

wherein the carbon atom which is provided with an * being the carbon atom in position 17 of the steroid skeleton and X is $H_2$, (H, 1-6 C acyloxy), (H, 1-6 C hydrocarbon radical) or O.

The invention also relates to pharmaceutical products which contain one or more of the compounds according to the invention as the active constituent. The new compounds can be administered orally or parenterally in the usual manner, in combination with pharmaceutical auxiliary substances, in the form of tablets, pills, dragees and other usual administration forms. The dosage forms can be prepared according to known galenical procedures. These pharmaceuticals are prepared according to generally known methods.

The administered amount of the compounds according to the present invention may vary within wide ranges, e.g. 50–1000 mg and preferably 100–800 mg during a therapy, which may last 1–10 days. If a one-day therapy is applied the amount administered may vary between e.g. 200 and 1000 mg. If on the other hand a longer therapy, e.g. 5 days, is applied the administered amount each day is lower, e.g. 10–200 mg.

The compounds according to the present invention are prepared by successively halogenating, dehydrohalogenating and hydrogenating oestrone 3-methyl ether or a corresponding 18-alkyl (1-3 C) compound at position 16.

The halogenation is preferably a bromination, in particular, performed with $CuBr_2$. This step is performed at 30°–100° C. under atmospheric pressure for 30–180 min.

The dehydrohalogenation is preferably a dehydrobromination, in particular, performed in the presence of lithium bromide, lithium carbonate and dimethylformamide. In general the reaction is terminated after 180 min. The temperature at which the reaction is performed is 60°–150° C. The hydrogenation takes place at 0°–80° C. under atmospheric pressure for 15–180 min. in the presence of a catalyst such as Pd/C.

The 17-ketone group in the $14\beta$ H-oestrone 3-methyl ether or the corresponding 18-alkyl (1-3 C) compound thus obtained is then reduced, for example with $NaBH_4$, to a $17\alpha$-OH group and the A ring is reduced to a $\Delta^2$, $\Delta^{5(10)}$ ring by means of a Birch reduction, for example by means of $Li/NH_3$/tetrahydrofuran. The 3-methoxy-$\Delta^2$, $\Delta^{5(10)}$-$14\beta$H-oestradien -$17\alpha$-ol or the corresponding 18-alkyl (1-3 C) compound is then converted with acid, for example oxalic acid, into $14\beta$H-$\Delta^{5(10)}$-$17\alpha$-OH-oestren-3-one or the corresponding 18-alkyl (1-3 C) compound which, after bromination and dehydrobromination, for example with phenyltrimethylammonium tribromide in pyridine, is converted into $14\beta$H$\Delta^4$, $\Delta^9$-$17\alpha$-OH-oestradien-3-one or the corresponding 18-alkyl (1-3 C) compound. Said compound is then ketalized, for example with ethylene glycol/$CH_2Cl_2$/triethyl orthoformate/p-toluenesulphonic acid to 3,3-ethylenedioxy-$14\beta$H-$\Delta^{5(10)}$, $\Delta^{9(11)}$-oestradien-$17\alpha$-ol or the corresponding 18-alkyl (1-3 C) compound.

The ketalization can also be performed so that compounds are obtained with the groups $-OR_6$ and $-OR_7$ in position 3, $R_6$ being an alkyl group containing 1-4 carbon atoms and R being an alkyl group containing 1-4 carbon atoms or $R_6$ and $R_7$ together forming an alkylene group containing 2-5 carbon atoms.

Starting from said compound, the desired substituents can be introduced at positions 17 and 11 in a manner known per se.

Thus, after epoxidation of the $\Delta^{5(10)}$ double bond, for example with m-chloroperbenzoic acid in $CH_2Cl_2$ and $NaHCO_3$, the $R_1$ group can be introduced with simultaneous formation of an OH group in position $5\alpha$ and displacement of the double bond from 9(11) to 9(10) by reaction With and $R_1$ -containing organometallic compound, such as $R_1MgBr$ or $R_1Li$, for example in the presence of CuCl in tetrahydrofuran. After oxidation of the $17\alpha$-OH group, for example by means of an oppenauer oxidation in cyclohexanone in the presence of aluminium triisopropoxide, a compound according to the present invention is obtained with $R_3$=OH by reaction with an $R_4$-Li or $R_4$-MgX (X can be a halogen atom) and subsequent dehydration and hydrolysis (for example in 80% acetic acid at 75° C. or in 2N HCl in acetone). It is also possible to dehydrate and hydrolyse immediately after the introduction of $R_1$; in that case compounds are obtained with $R_3$=OH and $R_4$=H.

Another method of preparing the compounds according to the present invention is to introduce first the groups in position 17 after the ketalization described above and then only the group $R_1$ in position 11. In that case the ketalized compound is first oxidized (yielding 17-keto) and reacted with an $R_4$-metal compound (yielding 17β-R4, 17α-OH) in order to be subsequently epoxidized and reacted with R1-MgB//CuCl. The compound should then be additionally dehydrated and hydrolysed (yielding 3-keto-Δ4). These steps are performed analogously to the corresponding steps already described.

A variant of the initial introduction of the groups in position 17 and then in position 11 is the following. First a group is introduced at 17β under the conditions already described above. This yields a corresponding compound with said group in position 17β and OH at 17α. The group R1 is then introduced in a manner analogous to that already described. If desired, any unsaturated bonds present in the group introduced at 17β are then reduced. Dehydration and hydrolysis is then carried out with simultaneous splitting off possible protective groups, such as, for example, tetrahydropyranyl ethers, in the 17β substituent to form compounds according to the present invention containing R4 at 17β and OH at 17α. The group to be introduced at 17β according to this variant is preferably an alkyl, alkenyl or alkynyl ether. Preference is given to groups with a terminal tetrahydropyranyl ether. In the step in which a part of the group introduced at 17β is split off, the tetrahydropyranyl group introduced at 17β is then split off to form an alkyl, alkenyl or alkynyl group with a terminal hydroxyl group. If desired, said group can be cyclized with the 17α-OH group.

Another method of preparing compounds according to the present invention is etherification of the 17-OH group after the ketalization already described and followed by introduction of the group R1 and dehydration and hydrolysis.

Yet another method is to introduce a group at position 11 which is such that the group R1 is formed in the final dehydration and hydrolysis. A suitable group is a phenyldioxane or phenyldioxolane; in the dehydration/hydrolysis step

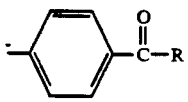

is then formed as group R1, wherein R=H or alkyl.

Yet another method of preparing compounds according to the present invention is to start from 3-methoxy-14βH-oestrone and successively perform a Wittig reaction using triphenylphosphonium methylide (yielding 17-methylene), to epoxidize (yielding 17,20-epoxy), to reduce with LiAlH4 (yielding 17β-OH, 17α-CH3) and then to introduce group R1 and to dehydrate/hydrolyse as has already been described. Starting from the 17-methylene compound hydrocarbyl groups comprising a hydroxy group may be introduced at position 17α, whereafter these compounds are converted into compounds according to the present invention in a way as already described.

After compounds according to the present invention have been obtained with R3 or R4=OH, said hydroxyl group may, if desired, be esterified or etherified by methods known in order to obtain other compounds according to the invention. Likewise OH groups in hydrocarbyl groups at position 17α or 17β may be esterified or etherified or, in addition, be oxidized.

The Δ 16- and 17-alkylidene compounds according to the present invention are obtained by dehydrating compounds according to the present invention comprising an OH group at position 17α or 17β.

As is evident from the foregoing, the compounds according to the invention are obtained by dehydrating and hydrolysing a compound having the formula:

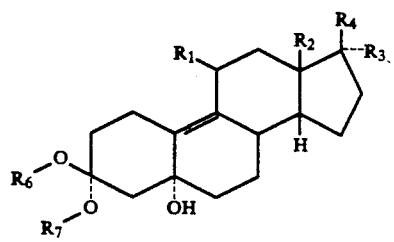

wherein R1, R2, R3 and R4 have the same meaning as has already been described, with the proviso that, if R1, R3 and/or R4 represent a group containing oxygen, R1, R3 and/or R4 may also be a group containing oxygen, the oxygen atom being protected by means of a hydrolysable group, and wherein R6 and R7 represent an alkyl group containing 1-4 carbon atoms or R6 and R7 together represent an alkylene group containing 2-5 carbon atoms, to form compounds according to the present invention. Preferably, the dehydration and the hydrolysis are performed in one step. The temperature at which this step is carried out is in general 10°-90° C.; the reaction time is usually 15 min. up to 16 hours. The dehydration/hydrolysis step is performed in a manner known per se and with agents known per se, such as, for example, with acetic acid or with HCl in acetone or in a mixture of toluene $-0.5N\ H_2SO_4$.

The invention is explained more in detail by means of the following examples.

EXAMPLE 1

200 g of $CuBr_2$ were added in several batches to a solution of 100 g of oestrone 3-methyl ether in a mixture of 800 ml of toluene and 800 ml of methanol. After 1 hour under reflux conditions, the mixture was filtered, diluted with 2 l of water and extracted with ether. The organic layer was washed, dried and concentrated. The residue was treated with 80%-aqueous ethanol. Yield: 117 g of 3-methoxy-16-bromooestra-1,3,5(10)-trien-17-one as a mixture of 16α and 16β bromides. To this, 170 g of LiBr, 150 g of $Li_2CO_3$ and 1 l of dimethylformamide were added. The mixture was stirred for 1 hour under reflux conditions. The mixture was then poured onto 5 l of water and extracted with ethyl acetate. The organic layer was washed several times with $H_2O$ and then dried and concentrated. The residue was passed through a silica-gel column using $CH_2Cl_2$ as the eluent.

8 g of 10% Pd/C were added to a solution of the product obtained from the eluate in 1.5 l of ethanol. Hydrogenation was then carried out until the calculated quantity of hydrogen had been absorbed. The catalyst was filtered off. The filtrate was concentrated and treated with 0.5 l of 50% aqueous ethanol. The precipitate was filtered and dried under vacuum at 50° C. until a constant weight was obtained. Yield: 75 g of 14β-3-methoxyoestra-1,3,5(10)-trien-17-one; melting point: 109°-110° C.

EXAMPLE 2

7 g of $NaBH_4$ were added in batches to a solution of 17 g of the compound obtained in the previous Example in a mixture of 350 ml of tetrahydrofuran and 350 ml of 96% aqueous ethanol. Stirring was then carried out for 1.5 hours at room temperature. The pH was then brought to 5 by carefully adding 50% aqueous acetic acid. The mixture was then concentrated to a small volume, diluted with water and extracted with $CH_2Cl_2$. The organic layer was successively washed with 1N NaOH, with 2N HCl and with water. Drying and concentration were then carried out and the residue was treated with a hexane/ether mixture. Yield: 15.6 g of (14β,17α)-3-methoxyoestra-1,3,5(10)-trien-17-ol; melting point: 102°-103° C. 4.8 g of lithium were added in small batches to a solution of 11 g of this compound in a mixture of 165 ml of tetrahydrofuran, 165 ml of tert.-butyl alcohol and 330 ml of liquid ammonia at −33° C. over a time period of approximately 3 hours. 40 ml of methanol were then added and the ammonia allowed to evaporate. The residue was diluted with water and extracted with $CH_2Cl_2$. The organic phase was washed, dried and concentrated. The residue was treated with hexane. In this manner, a white solid (melting point: 110°-112° C.) was obtained which was dissolved in a mixture of 250 ml of tetrahydrofuran and 100 ml of methanol. A solution of 9 g of oxalic acid dihydrate in 50 ml of water was added to this and stirring was then carried out for 6 hours. 50 g of $NaHCO_3$ were then added. The mixture was concentrated to a small volume. 250 ml of water were then added, and the product was extracted with $CH_2Cl_2$. The organic layer was washed, dried and concentrated. Yield: 9.4 g of (14β,17α)-17-hydroxyoestr-5(10)-en-3-one in the form of a viscous oil; $R_f$(toluene/ethyl acetate 7/3)=0.35. 40 g of phenyltrimethylammonium tribromide were added in batches to a solution of 31 g of this compound in 200 ml of pyridine in 10 min. After stirring for 3 hours at room temperature, the mixture was then poured into 2 l of water and the product was extracted with ethyl acetate. The combined organic layers were washed with 2N HCl and water. After drying and concentrating, the residue was treated with diisopropyl ether. After filtration and drying under vacuum, 18 g of (14β,17α)-17-hydroxyoestra-4,9-dien-3-one, melting point: 130°-131° C. were obtained.

A mixture of 17 g of this compound, 150 ml of $CH_2Cl_2$, 150 ml of ethylene glycol, 50 ml of triethyl orthoformate and 1 g of p-toluenesulphonic acid was stirred for 1 hour at room temperature and then boiled for 10 minutes. The reaction mixture was then treated with 20 g of solid $NaHCO_3$ and poured into 1 l of 5% $NaHCO_3$ solution. After extraction with ethyl acetate, and washing, drying and concentration of the organic layer, the residue was passed through a silica-gel column with hexane/ethyl acetate 3/1 (v/v) as eluent. In this manner, 18.5 g of (14β,17α)-17-hydroxy-3,3-ethylenedioxyoestra-5(10),9(11)-diene were obtained in the form of a colourless foam; $R_f$=0.56 (hexane/ethyl acetate 1/1).

EXAMPLE 3

25 g of $NaHCO_3$ were added to a solution of 18 g of the compound obtained in Example 2 in 100 ml of dry methylene chloride. A solution of 12.5 g of 80% m-chloroperbenzoic acid in 75 ml of methylene chloride was then added dropwise while stirring at −40° C. in 1 min. The mixture was then stirred on an ice-bath for 30 min. and poured into 500 ml of ice water. The product was extracted in methylene chloride. The organic layer was washed with a 5% $NaHCO_3$ solution and with water, and dried and concentrated. The residue was rapidly chromatographed on $SiO_2$ using hexane/ethyl acetate 2/1 (v/v) as eluent. This yielded 8.5 g of (5α,10α,14β,17α) -3,3-ethylene-dioxy-5,10-epoxyoestr-9(11)-en-17-ol in the form of a foam; $R_f$ 0.48 (hexane/ethyl acetate 1/1).

A Grignard reagent was prepared in 200 ml of dry tetrahydrofuran by reacting 24 g of p-bromo-N,N-dimethylaniline and 3 g of magnesium turnings. 300 mg of CuCl were added to this, followed by dropwise addition of 8.5 g of the epoxide in 30 ml of dry tetrahydrofuran. After stirring for 30 minutes at room temperature, the reaction mixture was poured into 1.5 l of a 10% $NH_4Cl$ solution and extracted in ethyl acetate. The organic layer was washed, dried and concentrated. The residue was chromatographed on $SiO_2$ using hexane/ethyl acetate 1/1 as eluent. After crystallization from diisopropyl ether, 6.6 g of (5α,11β,14β,17α)-3,3-ethylenedioxy-11-(4-dimethylaminophenyl)-oestr-9-ene-15,17-diol (melting point: 107°-109° C.) were obtained.

A solution of 1.5 g of this compound in 25 ml of 80% aqueous acetic acid was heated for 45 min. (75°-80° C.). The mixture was cooled with ice water and neutralized by adding concentrated $NH_4OH$. The product was extracted with ethyl acetate. The organic layer was washed, dried and concentrated. After treating the residue with diisopropyl ether, and crystallizing, filtering and drying the precipitate, 0.75 g of (14β,17α)-11-(4-dimethylaminophenyl)-17-hydroxyoestra-4,9-dien-3-one (melting point: 166°-167° C.; $a_D$ (dioxane)= +212°; $R_f$(hexane/ethyl acetate 1/1)=0.32) was obtained.

EXAMPLE 4

A solution of 4.8 g of (5α,11β,14β,17α)-3,3-ethylenedioxy-11-(4-dimethylaminophenyl)-oestr-9-ene-5,17-diol in a mixture of 200 m) of dry toluene, 40 ml of cyclohexanone and 6 g of aluminium isopropoxide was kept for 3 hours under reflux conditions. The mixture was cooled, diluted with 200 ml of ethyl acetate and washed several times with a 75% w/v solution of Seignette salt. The organic layer was finally washed with water, dried and concentrated. The residue was passed through a silica-gel column with a hexane/ethyl acetate gradient (10/1½) as eluent. The product was treated with a mixture of hexane and diisopropyl ether (½ v/v). The precipitate was filtered and dried. Yield: 3.1 g of (5α,11β,14β)-3,3-ethylenedioxy-5-hydroxy-11-(4-dimethylaminophenyl)-oestr-9-en-17-one (melting point: 158°-160° C.).

A solution of 3 ml of 1.5M $CH_3Li$-LiBr complex in ether was added dropwise to a solution of 2 g of this compound in 25 ml of dry tetrahydrofuran at −10° C. After stirring for 10 min., the mixture was poured into 100 ml of ice water. The product was extracted with ethyl acetate. The organic layer was washed, dried and concentrated. The residue was chromatographed on silica gel with a toluene/ethyl acetate gradient (10/1→½) as eluent. Yield: 1.2 g of amorphous (5α,11β,14β,17α) -3,3-ethylenedioxy-11-(4-dimethylaminophenyl)-17-methyloestr-9-ene-5,17-diol, $R_f$=0.42 (hexane/ethyl acetate 1/1). A solution of 1.2 g of this compound in 25 ml of 80% aqueous acetic acid was heated for 45 min. at 75° C. After cooling in ice water and neutralizing with concentrated $NH_4OH$, the product was extracted in ethyl acetate. The organic layer was washed, dried and concentrated. The residue was treated with 20 ml of diisopropyl ether. After crystallization the precipitate is filtered and dried. Yield: 0.73 g of (11β,14β,17α)-11-(4-dimethylaminophenyl)-17-hydroxy-17-methyloestra-4,9-dien-3-one (melting point=109°-111° C.; $\alpha_D$ (dioxane)=+213° and $R_f$=0.40 (hexane/ethyl acetate 1/1)). In an analogous way the corresponding 17β-ethynyl (m.p. 106°-107° C.) and 17β-1-propynyl ($R_f$=0.30 toluene/ethyl acetate 7/3 v/v) compounds were prepared.

The above 17-keto compound with m.p. 158°-160° C. was reacted with the Grignard reagent of 2-(2-bromoethyl)-1,3-dioxolane. The product obtained was converted with 80% acetic acid at 80° C. into (11β,14β,17α,5'R)-11-(4-dimethylaminophenyl)-17-hydroxy-17-(3-oxopropyl)-estra-4,9-dien-3-one, cyclic hemiacetal ($R_f$=0.30 hexane/ethylacetate). As a by-product (11β,14β,17α,5'R)-11-(4-dimethylaminophenyl -4',540 -dihydrospiro[estra-4 9-diene-17,2'(3'H) -5'-acetoxy-furan]-3-one (m.p. 199°-200° C.) was obtained.

EXAMPLE 5

29 g of dicyclohexylcarbodiimide were added to a solution of 16.5 g of the compound finally obtained in Example 2 in a mixture of 60 ml of toluene, 50 ml of dimethyl sulphoxide and 20 ml of pyridine. 5 ml of dichloroacetic acid were added dropwise at 5° C. in 10 min. A further amount of approximately 10 ml of pyridine was then added to keep the pH at 7. After stirring for 45 min., the excess of oxidant was destroyed by adding 5 ml of methanol dropwise, followed by a solution of 11 g of oxalic acid dihydrate in 50 ml of methanol. After stirring for 30 min., 500 ml of ether were added. After 30 min., the precipitate was filtered, the filtrate was washed several times with water, a 10% NaHCO₃ solution and water, and then dried and concentrated. The residue was chromatographed on SiO₂ with hexane/ethyl acetate 4/1 (v/v) as eluent. After treatment with hexane/diisopropyl ether, 9.8 g of (14β)-3,3-ethylenedioxyoestra -5(10),9(11)-dien-17-one (melting point: 110°-112° C.) were obtained.

20 ml of a 2M propyl magnesium chloride solution in ether were added to a solution of 7.5 g of propargyl alcohol tetrahydropyranyl ether in 50 ml of dry tetrahydrofuran. After stirring for 10 min., a solution of 4.75 g of the oestradienone compound prepared last in 20 ml of dry tetrahydrofuran was added to this. After stirring for 6 hours at room temperature, the reaction mixture was poured into 500 ml of a 10% NH₄Cl solution. The product was extracted with ethyl acetate. After washing, drying and concentrating the organic layer, the residue was chromatographed on silica gel using a hexane/ethyl acetate gradient (5/1→1/1) as eluent. Treatment of the product with diisopropyl ether/hexane 1/1 (v/v) yielded 4.1 g of (14β,17α)-3,3-ethylenedioxy-17-(3-tetrahydropyranyloxyprop-1-ynyl) oestra-5(10),9(11)-dien-17-ol (melting point: 130°-132° C.).

A solution of 4 g of 85% m-chloroperbenzoic acid in 100 ml of CH₂Cl₂ was added to a cooled (−60° C.) solution of 8.5 g of this compound and 10 g of solid NaHCO₃ in 100 ml of CH₂Cl₂. The mixture was stirred at 0° C. for 45 min. and then diluted with 250 ml of a 5% NaHCO₃ solution. The product was extracted in CH₂Cl₂ and the organic layer was washed several times with water. After drying and concentrating the residue was chromatographed on silica gel with a hexane/ethyl acetate gradient (4/1→1/1) as eluent. Yield: 5.8 g of amorphous (5α,10α,14β,17α)-3,3-ethylenedioxy-5,10-epoxy-17-(3-tetrahydropyranyloxyprop -1-ynyl)-oestr-9(11)-en-17-ol; $R_f$=0.63 (hexane/ethyl acetate 1/1).

A solution of 5.5 g of this compound in 20 ml of dry tetrahydrofuran was added to a Grignard reagent which had been prepared starting from 1.3 g of magnesium and 10.5 g of p-bromo-N,N-dimethylaniline in 60 ml of dry tetrahydrofuran and to which 300 mg of CuCl had been added. Stirring was then carried out for an additional one hour and the reaction mixture was then poured into 500 ml of a 10% NH₄Cl solution. After extraction with ethyl acetate and washing, drying and concentrating the organic phase, the residue was chromatographed on silica gel using hexane/ethyl acetate 3/2 as eluent. After treatment with hexane/-diisopropylether 1/2 (v/v), 4.5 g of (5α,11β,14β,17α)-3,3-ethylenedioxy-11-(4-dimethylaminophenyl) -17-(3-tetrahydropyranyloxyprop-1-ynyl)oestr-5-(10)-ene-5,17-diol, melting point: 161°-162° C. were obtained. A solution of 2 g thereof in a mixture of toluene/-ethanol 1/1 was hydrogenated in the presence of 200 mg of 5% pd-BaSO₄ until the theoretical quantity of 2 equivalents of hydrogen had been absorbed. The catalyst was filtered off and the filtrate concentrated. The residue was dissolved in 40 ml of 80% acetic acid and heated to 80° C. for 45 min. After cooling, the mixture was neutralized by addition of conc. NH₄OH and extracted with ethyl acetate. After washing, drying and concentrating the organic phase, the residue was chromatographed on silica gel with CH₂Cl₂/acetone 1/1 as eluent. Yield: 1.2 g of amorphous (11β,14β,17α)-11-(4-dimethylaminophenyl) -17-hydroxy-17-(3-hydroxypropyl)oestra-4,9-dien-3-one, $R_f$=0.42 (CH₂Cl₂/-acetone 1/1) and $\alpha_D$=+194° (c=1, dioxane).

Immediate dehydration and hydrolysis of the above 11-(4-dimethylaminophenyl)-17-(3-tetrahydropyranyloxyprop-1-ynyl) compound yielded the corresponding 17β-(3-hydroxyprop-1-ynyl) compound ($\alpha_D$+279° dioxane).

600 mg of p-toluenesulphonyl chloride were added to a solution of 1.2 g of this compound in 15 ml of pyridine. After stirring for 6 hours, 100 ml of H₂O were added. After extraction with ether, the organic layer was washed several times with H₂O, dried and concentrated. The residue was chromatographed on silica gel with toluene/acetone 2/1 as eluent. After treatment with hexane/isopropyl ether 1/1, 0.7 g of (11β,14β,17α)-11-(4-dimethylaminophenyl) -4',5'-dihydrospiro[oestra-4,9-diene-17,2'(3'H)-furan]-3-one (melting point: 172°-174° C.) was obtained.

To a solution of 500 mg of this compound in 10 ml CH₂Cl₂ and 1 g CaO a solution of 700 mg I₂ in 10 ml CH₃OH was added. After stirring for 3 h. at room temperature the mixture was poured onto 200 ml 5% NaHSO₃ and extracted with ethyl acetate. After washing, drying and evaporating the organic phase the residue was chromatographed on silica gel. This yielded 140 mg of the corresponding 4-methylamino-phenyl compound (m.p. 120°-122° C.).

In an analogous way as described for the 4-dimethylaminophenyl compound the corresponding 4-diethylaminophenyl compound was obtained (m.p. 135°-137° C.).

To a solution of the 17α-hydroxy-17β-(3-hydroxypropyl) compound with $\alpha_D$=+194° C. in a mixture of toluene (3 ml), CH₂Cl₂ (3 ml), dimethylsulphoxyde (2 ml) and pyridine (0.4 ml) 0.7 g of dicyclohexyl-carbodiimide was added. Subsequently 0.11 ml dichloro-acetic acid was added dropwise at 0° C. After 0.5 h. 0.1 ml of methanol was added dropwise followed by 0.26 g oxalic acid in 1 ml of methanol. After stirring for 15 min. the mixture was diluted with 30 ml of ether. The precipitate was filtered off and the organic phase was washed, dried and concentrated. The residue was chromatographed on silica gel. This yielded 250 mg of (11β,14β)-11-(4-dimethylaminophenyl]-17-(3-hydroxypropyl)estra-4,9,16-trien-3-one (R$_f$=0.29 hexane/ethylacetate 1/1 v/v) and some (11β,14β)-11-(4-dimethylaminophenyl)-17-(3-hydroxypropylidene)estra-4,9-dien-3-one (R$_f$=0.29 hexane/ethylacetate 1/1 v/v).

Starting from 18-methyloestrone 3-methylether examples 1, 2 and 5 were repeated in an analogous way yielding (11β,14β,17α)-11-(4-dimethylaminophenyl)-17-hydroxy-17-(3-hydroxypropyl)-18-methylestra-4,9-dien-3-one (R$_f$=0.17; toluene/acetone 3/1 v/v) and (11β,14β,17α)-11-(4-dimethylaminophenyl)-18-methyl-4′,5′-dihydrospiro[estra-4,9-dien-17,2′(3′H)-furan]-3-one (m.p 151°-152° C.).

EXAMPLE 6

3 g of a 50% dispersion of sodium hydride in mineral oil were added to a solution of 5 g of the compound finally obtained in Example 2 in a mixture of 50 ml of tetrahydrofuran and 20 ml of dimethyl sulphoxide. After stirring for 5 min., 5 ml of ethyl iodide were added. The reaction, which was followed by means of thin-layer chromatography, had proceeded to completion after 3 hours. The mixture was poured into water and the product was extracted with ether. After washing, drying and concentrating of the organic solvent, the residue was chromatographed on silica gel using hexane/ethyl acetate 95/5 (v/v) as eluent. Yield: 5.1 g of (14β,17α)-3,3-ethylenedioxy -17-ethoxyoestra-5(10),9(11)-diene in the form of a colourless oil; R$_f$=0.34 (hexane/ethyl acetate).

7 g of sodium bicarbonate were added to a solution of 4.2 g of this compound in 50 ml of dry methylene chloride and then a solution of 2 g of 80% m-chloroperbenzoic acid in 25 ml of methylene chloride was added at −40° C. After stirring for 30 min. at 0° C., the mixture was poured into 200 ml of a 5% sodium bicarbonate solution. After extraction with methylene chloride, the organic phase was washed, dried and concentrated. The residue was chromatographed on silica gel using hexane/ethyl acetate 9/1 as eluent. The product obtained was treated with the Grignard reagent p-dimethylaminophenylmagnesium bromide in the presence of 150 mg of CuCl in 40 ml of tetrahydrofuran. After stirring for 30 min. at room temperature, the reaction mixture was poured into 300 ml of a 10% NH$_4$Cl solution. After extraction with ether, the organic phase was washed, dried and concentrated. The residue was chromatographed on silica gel using hexane/ethyl acetate 3/2 as eluent. Yield: 2.4 g of (5α,11β,14β,17α)-3,3-ethylenedioxy-11-(4-dimethylaminophenyl) -17-ethoxyoestr-9-en-5-ol in the form of a colourless oil; R$_f$=0.59 (hexane/ethyl acetate 1/1, v/v. A solution of 2.2 g of this compound in 50 ml of 80% acetic acid was heated for 1 hour at 80° C. After cooling, the reaction mixture was neutralized with concentrated ammonia. After extraction with ether, the organic phase was washed, dried and concentrated. The residue was chromatographed on silica gel using hexane/acetone 9/1 as eluent. Yield: 1.3 g of (11β,14β,17α) -11-(4-dimethylaminophenyl)-17-ethoxyoestr-4,9-dien-3-one in the form of a yellowish oil; R$_f$=0.33 (hexane/acetone 9/1).

In an analogous way the corresponding 17α-butyloxy (α$_D$163°, dioxane) and 17α-hexyloxy (α$_D$ 153°, dioxane) compounds were prepared.

EXAMPLE 7

300 mg of CuCl were added to the Grignard reagent prepared from 4.5 g of 4-(5,5-dimethyl-1,3-dioxan-2-yl)phenyl bromide and 0.8 g of Mg in 15 ml of dry tetra-hydrofuran, followed by 2.2 g of (5α,10α,14β,-17α)-3,3-ethylenedioxy-5,10-epoxyoestr-9(11)-en-17-ol, prepared in Example 3, in 10 ml of dry tetrahydrofuran. After stirring for 1 hour at room temperature, the mixture was poured into 200 ml of saturated NH$_4$Cl solution. After extraction with ethyl acetate and washing, drying and concentrating the organic phase, the residue was chromatographed on silica gel using hexane/ethyl acetate 1/1 as eluent. After crystallization from diisopropyl ether, 1.7 g of (5α,11β,14β,17α)-3,3-ethylenedioxy-11[4-(5,5-dimethyl-1,3-dioxan-2-yl) phenyl]oestr-9-ene-5,17-diol were obtained; melting point: 176°-177° C. A solution of 1.5 g of this compound in 30 ml of 80% acetic acid was heated for 45 min. at 75° C. After cooling and neutralizing by concentrated NH$_4$OH, the product was extracted with ethyl acetate. The organic phase was washed, dried and concentrated. The residue was chromatographed on silica gel using hexane/ethyl acetate 1/1 as eluent. After crystallization from diisopropyl ether, 0.6 g of (11β,14β,17α)-11-(4-formylphenyl)-17-hydroxyoestra-4,9-dien-3-one was obtained; melting point: 153°-155° C.

EXAMPLE 8

Oxidation of 1.25 g of the oestrenediol compound prepared in Example 7 with 2 g of aluminium isopropoxide in a mixture of 60 ml of toluene and 10 ml of cyclohexanone under reflux conditions yielded, after crystallization from ether/hexane, 0.95 g of (5α,11β,14β)-3,3-ethylenedioxy-11-[4-(5,5-dimethyl-1,3-dioxan-2-yl)phenyl]-5-hydroxyoestr-9-en-17-one, melting point: 158°-160° C. This product was ethinylated with lithium acetylide in tetrahydrofuran, and 0.4 g of the material obtained was dissolved in 5 ml of 80% aqueous acetic acid and heated for 1 hour at 75° C. After cooling and neutralizing with a concentrated NH$_4$OH solution, the product was extracted with ether. After Washing, drying and concentrating the organic layer, the residue was chromatographed on silica gel with hexane/ethyl acetate 1/1 as eluent. After crystallization from diisopropyl ether, 210 mg of (11β,14β,17β)-11-(4-formylphenyl)-17-hydroxypregna -4,9-dien-20-yn-3-one were obtained; melting point: 223°-225° C.

In an analogous way to that described in Example 7 and this Example the corresponding 11-(4-acetylphenyl) compound (m.p. 179°-180° C.) was prepared.

In an analogous way to that described in Example 7 and the oxidation step in this Example, followed by incorporation of the 3-tetrahydropyranyloxyprop-1-ynyl group at position 17 and cyclizing as described in Example 5, (11β,14β,17α)-11-(4-acetylphenyl)-4′,5′-dihydrospiro[oestra -4,9-diene-17,2′(3′H)-furan]-3-one (α$_D$ 165° in dioxane) was obtained.

EXAMPLE 9

A mixture of 4 g 14β-oestron-3-methylether, 2.2 g LiNH$_2$ and 38 g methyltriphenylphosphoniumbromide in 130 ml toluene and 10 ml dimethylsulphoxide was heated at 60° C. for 16 h. Subsequently, the mixture was poured out into 300 ml ice-water and extracted with ethylacetate. Purification by chromatography yielded the corresponding 17-methylene compound. To a solution of 11.2 g of this compound in 200 ml dry tetrahydrofuran 100 ml of 0.5 molar 9-borabicyclononane in tetrahydrofuran was added dropwise at room temperature. The mixture was stirred for 1 h. at room temperature. Subsequently 80 ml of H₂O, 80 ml of 3N NaOH and 40 ml 3o% H₂O₂ were added dropwise after each other. After 2 h. this was poured into water and the product was extracted by means of ethyl acetate. The residue obtained after washing, drying and evaporation was triturated with diisopropylether yielding the corresponding 17α-hydroxymethyl compound. This compound was converted into the 3,3-ethylenedioxy-▲$^{5(10)}$, ▲$^{9(11)}$ derivative as described in Example 2. A part of this derivative (2.4 g) was converted into the 17α-methoxymethyl derivative by dissolving it in a mixture of 84 ml tetrahydrofuran and 15 ml dimethylsulphoxide, and reacting with 4.8 g 50% NaH dispersion in oil and 3.6 ml methyliodide. After stirring for 16 h at room temperature, the mixture was poured into ice-water, extracted with ether, washed, dried, evaporated and chromatographed.

Analogously to the procedure described in Example 3 these 17α-hydroxymethyl and 17α-methoxymethyl compounds were converted into (11β,14β,17α)-11-(4-dimethylaminophenyl) -17-hydroxymethyl-estra-4,9-dien-3-one (m.p. 185 methoxymethyl-estra-4,9-dien-3-one ($\alpha_D$= +214° C.=1, dioxane) respectively. The first compound was reacted with acetic acid anhydride in pyridine at room temperature yielding the corresponding acetic acid ester (m.p. 142° C.).

EXAMPLE 10

A mixture of 60 g of K-t.butylate and 256 g ethyltriphenylphosphonium iodide in 1200 ml tetrahydrofuran was stirred for 0.5 h at room temperature. Subsequently 87 g of 14β-oestrone-3-methylether in 600 ml of tetrahydrofuran was added. The mixture was left at reflux temperature for 10 h. and subsequently poured out into 6 l of H₂O and extracted with ethyl acetate. Chromatography of the product on silica gel yielded 104 g of the corresponding 17-Z/E-ethylidene (5/1) compound. To a solution of 106 ml 10M BH₃.dimethylsulphide complex in 400 ml of tetrahydrofuran 131 ml 1,4-cyclooctadiene was added dropwise at 0° C. After keeping this 1 h. at reflux temperature 140 g of the above 17-Z/E-ethylidene product in 400 ml of tetrahydrofuran was added at room temperature. Subsequently this was kept at reflux temperature for 3 h. Then 484 ml 3 N NaoH and 484 ml 30% H₂O₂ were added successively. The mixture was poured into 7 l 10% Na₂SO₃ solution and extracted with ethylacetate. Chromatography yielded 17 g of (14β,17α,20S)-20-hydroxy-pregna-1,3,5(10)-triene and 70 g of (14,17α,20R)-20-hydroxy-pregna-1,3,5(10)-triene. These compounds Were converted into (11β,14β,17α,20S)-11-(4-dimethylaminophenyl) -20-hydroxy-pregna-4,9-dien-3-one (m.p. 210°–212° C.) and (11β,14β,17α,20R)-11-(4- dimethylaminophenyl) -20-hy-droxy-pregna-4,9-dien-3-one ($\alpha_D$= +166° C.=1, dioxane) by methods described in Examples 2 and 3.

Oxidation of the 20R-compound yielded the corresponding 20-keto compound ($\alpha_D$=215° C.=1, dioxane). Esterification of the 20R- and 20S-compound by means of propionic acid anhydride yielded the corresponding 20-R-propionate ($\alpha_D$=176° C.=1, dioxane) and 20-S-propionate ($\alpha_D$= +227° C.=1, dioxane) respectively.

EXAMPLE 11

The following compounds were tested in a pregnancy interruption test and an antiglucocorticoid test:

compound 1: (11β,14β,17α)-11-(4-dimethylaminophenyl) -4',5'-dihydrospiro[oestra-4,9-diene-17,2'(3'H)-furan]-3-one (according to the present invention).

compound 2: (11β,17α)-11-(4-dimethylaminophenyl)-17-hydroxy-17-(1-propynyl)-oestra-4,9-dien-3-one.

compound 3: (11β,13α,17α)-11-(4-dimethylaminophenyl) -17-hydroxy-17-(3-hydroxy-propyl)-oestra-4,9-dien-3-one.

The pregnancy interruption test was carried out in a similar way as described in Contraception 1981, Vol. 24, No. 3, page 289–299: pregnant rats were given 2 times a day an amount "X" of one of the above compounds orally from the 6th until the 10th day of the pregnancy. At the 15th day the rats were sacrificed and the following figure was determined:

$$P = \frac{(\text{total amount of implantation points} - \text{total amount of living embryo's})100}{\text{total amount of implantation points}}$$

The antiglucocorticoid test was performed as follows. Young male rats were given orally 5 μg/day of dexamethasone (group 1) or 5 μg/day of dexamethasone+1 mg/day of one of the above compounds (group 2) or nothing (only vehicle medium) (group 3) during 7 days. The following day the rats were sacrificed, the thymus of the rats was weighed and the following figure was calculated:

$$Q = \frac{\text{thymus weight group 2} - \text{thymus weight group 1}}{\text{thymus weight group 3} - \text{thymus weight group 1}}$$

(the lower Q the lower is the antiglucocorticoid activity).

The results are presented in the following Table:

TABLE

|  | P at X = 0.5 mg | P at X = 1 mg | Q |
|---|---|---|---|
| compound 1 | 96 | 100 | 5 |
| compound 2 | — | 100 | 92 |
| compound 3 | 49 | 100 | 70 |

What is claimed is:
1. An 11-arylsteroid derivative having the structure:

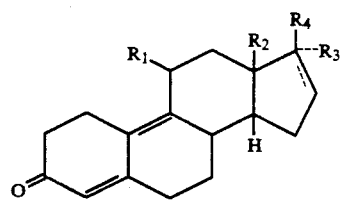

wherein:
R₁ is a homocyclic or heterocyclic aryl group having one of the following substituents: a saturated or unsaturated, branched or unbranched hydrocarbon radical containing 1–10 carbon atoms;
R₂ is an alkyl group containing 1–4 carbon atoms;

R₃ is H, OH, a saturated or unsaturated hydrocarbon radical containing 1–8 carbon atoms, an (1–18 C) acyloxy, (2–8 C) alkoxyalkyl, (1–18 C) acyl or (1–12 C) alkoxy group;

R₄ is H, OH, a saturated or unsaturated hydrocarbon group containing 1–8 carbon atoms, an (1–18 C) acyloxy, (2–8 C) alkoxyalkyl (1–18 C) acyl or (1–12 C) alkoxy group; or R³ and R₄ together form a ring system or an alkylidene group having 1–6 carbon atoms and the dotted line represents an optional bond between the carbon atoms 16 and 17 of the steroid skeleton, with the proviso that R₃ or R₄ is absent if said bond between said carbon atoms 16 and 17 is present.

2. A compound according to claim 1, wherein R₂ is methyl or ethyl.

3. A compound according to claim 1, wherein R₃ represents OH, (1–8 C) alkoxy, (1–6C) acyl, (1–6 C) alkyl, (1–6C) alkyl provided with a hydroxyl group, or alkoxyalkyl with the formula $C_nH_{2n+1}OC_mH_{2m}$, wherein n=1–3 and m=1–3.

4. A compound according to claim 1, wherein R₄ represents H, (1–6 C) hydrocarbyl, or (1–6 C) hydrocarbyl provided with a hydroxyl group.

5. A compound according to claim 1, wherein R₃ is a hydrocarbon radical containing 1–8 carbon atoms having at least one substituent selected from the group consisting of hydroxyl, azido, nitrile, oxo and halogen groups, wherein if more than one substituent is selected they may be the same or different.

6. A compound according to claim 1, wherein R₄ is a hydrocarbon group containing 1–8 carbon atoms having at least one substituent selected from the group consisting of hydroxyl, azido, nitrile, oxo and halogen groups, wherein if more than one substituent is selected they may be the same or different.

7. Method for preparing compounds according to claim 1, characterized in that a compound having the formula:

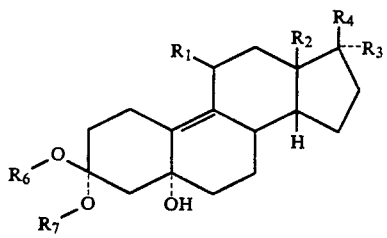

wherein R₁, R₂, R₃ and R₄ have the same meaning as in claim 1, with the proviso that if R₁, R₃ and/or R₄ represent an oxygen-containing group, R₁, R₃ and/or R₄ may also be an oxygen-containing group, the oxygen atom being protected by means of a hydrolysable group, and wherein R₆ and R₇ represent an alkyl group containing 1–4 carbon atoms or R₆ and R₇ together represent an alkylene group containing 2–5 carbon atoms, is dehydrated and hydrolysed to form compounds according to claim 1 and that subsequently, if desired, compounds comprising an OH group at position 17α or 17β are dehydrated, esterified or etherified and, if desired, compounds comprising a hydrocarbon radical provided with one or more hydroxyl groups are esterified, etherified or oxidized.

8. Pharmaceutical composition comprising an effective amount of a compound according to claim 1 to effect anti-progestinic activity and a pharmaceutically acceptable carrier.

9. An 11-arylsteroid derivative having the structure:

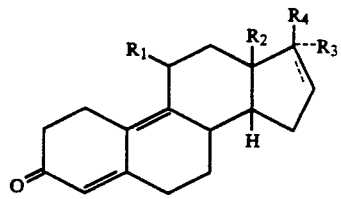

wherein:

R₁ is a homocyclic or heterocyclic aryl group having one of the following substituents: a saturated or unsaturated, branched or unbranched hydrocarbon radical containing 1–10 carbon atoms, said hydrocarbon radical having at least one substituent selected from the group consisting of hydroxyimino, oxo, hydroxyl and

, wherein X and Y are each separately H or a (1–4 C) hydrocarbon radical, or together comprise a (2–6 C) hydrocarbon radical;

R₂ is an alkyl group containing 1–4 carbon atoms;

R₃ is H, OH, a saturated or unsaturated hydrocarbon radical containing 1–8 carbon atoms, a saturated or unsaturated hydrocarbon radical containing 1–8 carbon atoms having at least one substituent selected from the group consisting of hydroxyl, azido, nitrile, oxo, halogen, (1–18 C) acyloxy, (2–8 C) alkoxyalkyl, (1–18 C) acyl and (1–12 C) alkoxy groups;

R₄ is H, OH, a saturated or unsaturated hydrocarbon group containing 1–8 carbon atoms, a saturated or unsaturated hydrocarbon radical containing 1–8 carbon atoms having at least one substituent selected from the group consisting of hydroxyl, azido, nitrile, oxo, halogen (1–18 C) acyloxy, (2–8 C) alkoxyalkyl, (1–18 C) acyl and (1–12 C) alkoxy groups; or wherein R³ and R₄ together form a ring system of an alkylidene group having 1–6 carbon atoms and the dotted line represents an optional bond between the carbon atoms 16 and 17 of the steroid skeleton, with the proviso that R₃ or R₄ is absent if said optional bond between said carbon atoms 16 and 17 is present.

10. A compound according to claim 9, wherein R₁ is an aryl group containing as substituent an acyl group having 1–4 carbon atoms or a group

wherein X and Y separately are H or a saturated alkyl group having 1–3 carbon atoms.

* * * * *